(12) United States Patent
Iwata et al.

(10) Patent No.: US 8,968,563 B2
(45) Date of Patent: Mar. 3, 2015

(54) FRACTIONATING AND REFINING DEVICE

(75) Inventors: Yosuke Iwata, Miyazaki-cho (JP); Tomoyuki Yamazaki, Saiin-Syumei-cho (JP); Przemyslaw Stasica, Hertfordshire (GB); Bob Boughtflower, Essex (GB)

(73) Assignee: Shimadzu Corporation, Kyoto-shi (JP)

( * ) Notice: Subject to any disclaimer, the term of this patent is extended or adjusted under 35 U.S.C. 154(b) by 599 days.

(21) Appl. No.: 13/262,524

(22) PCT Filed: Mar. 31, 2009

(86) PCT No.: PCT/JP2009/056596
§ 371 (c)(1),
(2), (4) Date: Sep. 30, 2011

(87) PCT Pub. No.: WO2010/113241
PCT Pub. Date: Oct. 7, 2010

(65) Prior Publication Data
US 2012/0018100 A1 Jan. 26, 2012

(51) Int. Cl.
*G01N 30/80* (2006.01)
*B01D 15/24* (2006.01)
*G01N 30/84* (2006.01)

(52) U.S. Cl.
CPC .............. *G01N 30/80* (2013.01); *B01D 15/24* (2013.01); *G01N 30/84* (2013.01); *G01N 2030/8447* (2013.01); *G01N 2030/8494* (2013.01)
USPC ...................................... 210/198.2; 159/4.01

(58) Field of Classification Search
CPC ................................................ G01N 30/8447
See application file for complete search history.

(56) References Cited

U.S. PATENT DOCUMENTS

| 6,384,411 B1 * | 5/2002 | Hirabayashi et al. ......... 250/288 |
| 6,413,428 B1 | 7/2002 | Berger et al. |
| 6,652,753 B2 | 11/2003 | Klein et al. |

(Continued)

FOREIGN PATENT DOCUMENTS

| CN | 2200818 Y | 6/1995 |
| JP | 60-253867 A | 12/1985 |

(Continued)

OTHER PUBLICATIONS

GEA Pharma Systems. Fluidized Spray Dryer—FSD—Combines spray drying and fluid bed drying technologies. WayBackMachine date Mar. 20, 2008. available at <http://www.niro.com/niro/cmsdoc.nsf/WebDoc/ndkk5hmchf.*

(Continued)

*Primary Examiner* — Katherine Zalasky
*Assistant Examiner* — Kara Graber
(74) *Attorney, Agent, or Firm* — Westerman, Hattori, Daniels & Adrian, LLP

(57) ABSTRACT

A fractionating and refining device includes a solution sending flow path for supplying a solution, including a fractionated target component, a gas supply flow path, a collecting vessel, a warming mechanism for warming the collecting vessel, and a probe formed by integrating tip end portions of the solution sending flow path and the gas supply flow path with each other. A lid of the vessel includes a solution inlet to which the tip end portion of the solution sending flow path is connected, gas inlets to which the tip end portion of the gas supply flow path is connected, and gas discharge ports connecting an inside and an outside of a vessel main body of the vessel.

6 Claims, 3 Drawing Sheets

(56) References Cited

U.S. PATENT DOCUMENTS

| | | |
|---|---|---|
| 6,656,354 B2 | 12/2003 | Berger et al. |
| 6,685,828 B2 | 2/2004 | Berger et al. |
| 2002/0122745 A1 | 9/2002 | Takase et al. |
| 2002/0139752 A1 | 10/2002 | Berger et al. |
| 2003/0019812 A1 | 1/2003 | Berger et al. |
| 2005/0031692 A1* | 2/2005 | Beyerinck et al. ............ 424/486 |
| 2006/0108285 A1 | 5/2006 | Bounoshita et al. |

FOREIGN PATENT DOCUMENTS

| | | |
|---|---|---|
| JP | 2-122260 A | 5/1990 |
| JP | 10-300740 A | 11/1998 |
| JP | 2002-202316 A | 7/2002 |
| JP | 2003-149217 A | 5/2003 |
| JP | 2006-136838 A | 6/2006 |
| JP | 2008-058324 A | 3/2008 |

OTHER PUBLICATIONS

Chinese Office Action dated Sep. 11, 2013, issued in Chinese Patent Application No. 200980158451.5, w/English translation.

International Search Report of PCT/JP2009/056596, mailing date May 19, 2009.

* cited by examiner

FRACTIONATING AND REFINING DEVICE

BACKGROUND OF THE INVENTION

1. Field of the Invention

The present invention relates to a fractionating and refining device for separating a target component from a solution and collecting it as solid material by a liquid chromatograph in order to use the target component included in the solution as a sample for obtaining data to be stored as a library or as a sample for a detailed analysis in a field such as a pharmaceutical field.

2. Description of the Related Art

As a fractionating and refining device using a liquid chromatograph, there is a device for separating target components (compounds) in a sample solution by the liquid chromatograph, respectively introducing them into separate trap columns to temporarily trap them, and allowing solvents to flow through the respective columns to elute the components trapped in the trap columns to thereby condense and collect the target components (refer to Patent Documents 1 and 2).

Because solutes fractionated by the liquid chromatograph are dissolved in the solution, they are normally powderized over hours by using an evaporator or the like. In a drug discovery step in a pharmaceutical field, drug candidates are separated, refined, and powderized to be used for a metabolism study, a drug production study, a physical property study, and the like which are latter steps.

However, the powderization by the evaporator disadvantageously requires a long time.

Patent Document 1: Japanese Patent Laid-open Publication No. 2-122260

Patent Document 2: Japanese Patent Laid-open Publication No. 2003-149217

SUMMARY OF THE INVENTION

It is an object of the present invention to provide a fractionating and refining device used for a solution including a target component separated and fractionated by a column of a fractionating liquid chromatograph or a solution obtained by temporarily trapping a target component separated by a column of a liquid chromatograph into a trap column and then eluting it again into a solvent different from a mobile phase in the liquid chromatograph, the device capable of collecting the target component as solid material from the solution in a short time.

A fractionating and refining device according to the present invention includes: a solution sending flow path for supplying a solution including a fractionated target component from a tip end thereof; a gas supply flow path for supplying gas from a tip end thereof; a collecting vessel; and a warming mechanism for warming the collecting vessel to such a temperature so as to facilitate evaporation of a solvent in the solution in the vessel. The collecting vessel is a collecting vessel including a vessel main body having a bottom and a lid which closes an opening portion of the vessel main body and which can be opened and closed, the lid including a solution inlet to which the tip end portion of the solution sending flow path is connected and through which the solution from the solution sending flow path is supplied into the vessel main body, a gas inlet to which the tip end portion of the gas supply flow path is connected and through which the gas from the gas supply flow path is supplied into the vessel main body, and a gas discharge port connecting an inside and an outside of the vessel main body.

The solution including the target component may be an eluting solution itself separated in a column of a liquid chromatograph and collected so as to include a specific target component or may be an eluting solution including the target component and obtained by temporarily trapping the separated specific target component in a trap column and then supplying a solvent having high eluting performance to the trap column to thereby elute the component again.

The gas supplied from the gas supply flow path into the collecting vessel is nebulizing gas for nebulizing the solvent including a solute. The gas warms the collecting vessel to thereby facilitate evaporation of droplets of solvent heated on an inner surface of the collecting vessel. As such gas, inert gas is generally suitable, and, for example, helium, argon, nitrogen, and the like can be used. Air may be used if the target component is a component which is not oxidized.

The warming temperature of the collecting vessel by the warming mechanism may be about a boiling point of the solvent to be evaporated. If the solvent is an organic solvent, such as dichloromethane having a low boiling point (about 40° C. in a case of dichloromethane), the vessel may be warmed to about 40° C.

The solution from the solution sending flow path drops or flows down into the vessel main body from the tip end portion of the solution sending flow path through the solution inlet in the lid. At this time, the gas is supplied from the tip end portion of the gas supply flow path into the vessel main body through the gas inlet in the lid, and therefore, the solution turns into minute droplets which adhere to an inner wall of the vessel main body. Because the vessel main body is warmed, the solvent in the droplets adhering to the inner wall of the vessel main body quickly evaporates and the target component is deposited on the inner wall of the vessel.

The gas supplied from the gas supply flow path into the vessel main body goes outside from the gas discharge port after turning the solution into the minute droplets and facilitating the evaporation of the solvent. Because the opening portion of the vessel main body excluding the gas discharge port is not open but closed with the lid, it is possible to suppress discharge of the powderized solute to the outside of the vessel by the gas to thereby suppress scattering of the target component.

In order to facilitate operation for mounting the collecting vessel to the fractionating and refining device, it is preferable to further include a probe formed by integrating the tip end portion of the solution sending flow path and the tip end portion of the gas supply flow path with each other. The solution inlet and the gas inlet in the lid are disposed in positions respectively corresponding to the tip end portion of the solution sending flow path and the tip end portion of the gas supply flow path integrated in the probe so that the tip end portion of the solution sending flow path and the tip end portion of the gas supply flow path are respectively connected to the solution inlet and the gas inlet in the lid when the probe is mounted to the lid.

More preferably, the tip end portion of the probe is made up of a double tube and one tube of the double tube is connected to the solution sending flow path while the other is connected to the gas supply flow path. In this case, the solution inlet and the gas inlet in the lid are preferably formed as one central inlet disposed at a center of the lid and corresponding to a central outlet of the double tube and a plurality of outer inlets disposed around the central inlet and on a circumference corresponding to an outer outlet of the double tube.

In an example of the probe having the tip end portion made up of the double tube, the inner tube of the double tube is connected to the solution sending flow path and the outer tube of the double tube is connected to the gas supply flow path. In this case, even if a flow rate of the solution supplied from the solution sending flow path is low, the solution drops into the collecting vessel from the central inlet disposed at the center of the lid and gas is supplied from positions around the central inlet.

If the probe is provided, the solution and the gas are supplied into the collecting vessel from the central portion of the lid and the gas discharge ports are provided on an outer peripheral side of these inlets. As a preferable example of placement of the gas discharge ports, the plurality of gas discharge ports are provided in the lid and disposed at equal intervals on a circumference outside the circumference on which the outer inlets out of the solution inlet(s) and the gas inlet(s) are disposed.

The higher the temperature of the gas blowing on the solution in the collecting vessel, the more efficiently it is possible to evaporate the solvent. Therefore, it is preferable to include gas heating means on the gas supply flow path.

Moreover, the higher the temperature of the solution dropping or flowing down into the collecting vessel from the solution inlet in the lid, the more efficiently it is possible to evaporate the solvent when a flow of gas scatters the solvent or when the flow of gas blows on the solvent. Therefore, it is preferable to include solution heating means on the solution sending flow path.

In the fractionating and refining device of the present invention, because the solution including the target component drops or flows down into the warmed collecting vessel from the solution sending flow path and the gas is supplied into the collecting vessel, the solvent in the solution is evaporated quickly and the target component is powderized and collected quickly. At this time, because the collecting vessel has the lid, it is possible to suppress scattering of the target component to thereby increase a collecting rate of the target component.

DESCRIPTION OF THE REFERENCE NUMERALS

Figure 1:
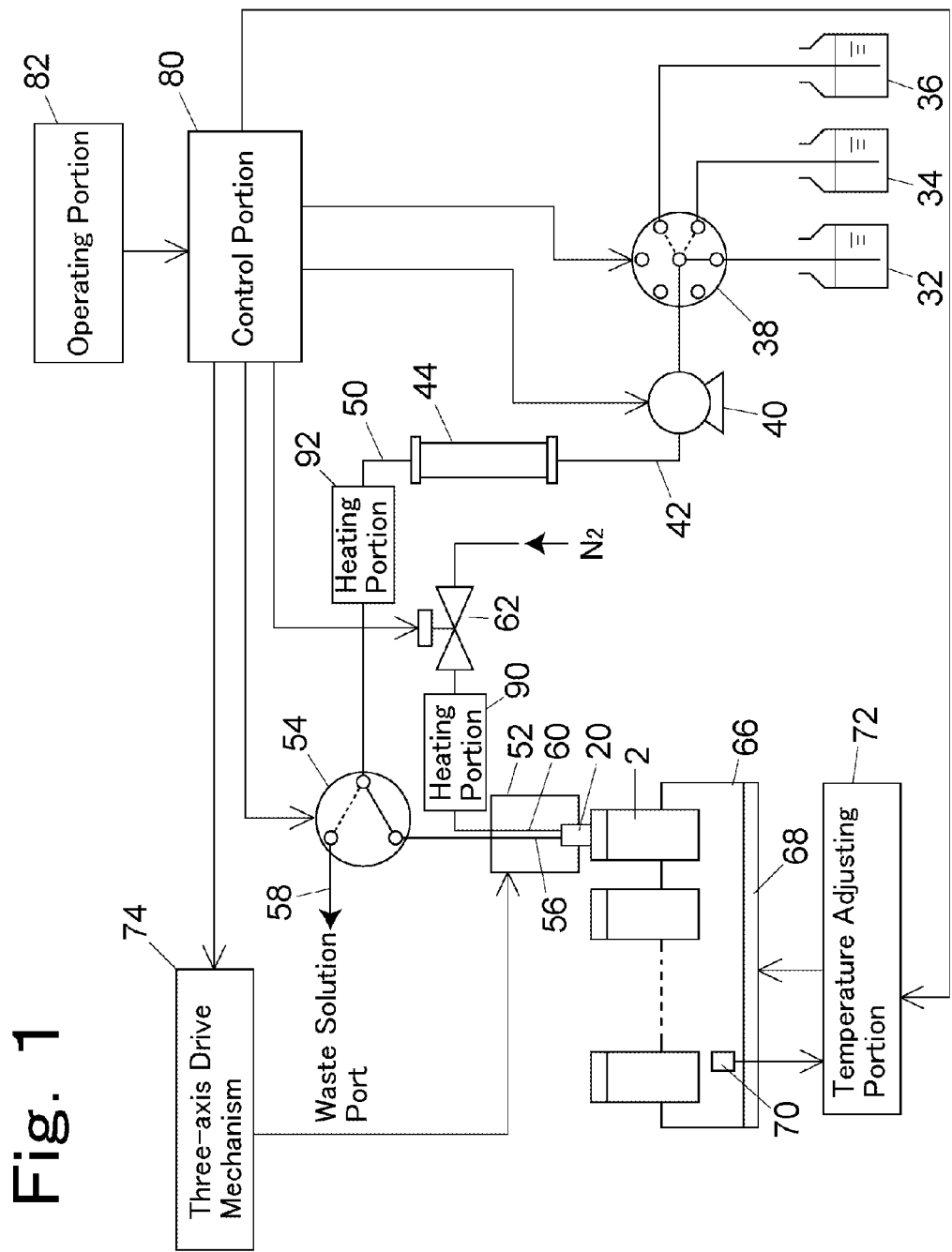
FIG. 1 is a schematic block diagram showing an embodiment.

2: Collecting vessel
4: Lid
8: Solution inlet
10: Gas inlet
12: Gas discharge port
20: Probe
32: Solution vessel
36: Eluting solvent vessel
44: Trap column
56: Fractionating flow path as solution sending flow path
66: Vessel rack
68: Heater

DETAILED DESCRIPTION OF THE INVENTION

An embodiment will be described with reference to FIGS. 1 to 4.

A solution sending device for supplying a solution including a fractionated target component from its tip end is for refining, in a trap column 44, a target compound in the solution in a solution vessel 32 including the target compound fractionated in advance by a fractionating liquid chromatograph (not shown) and supplying the target compound.

In FIG. 1, the solution including the target compound fractionated in advance is stored in the solution vessel 32. A solvent of the solution is a mobile phase used in the fractionating liquid chromatograph. Pure water is stored as cleaning water in a cleaning water vessel 34 and dichloromethane is stored as an eluting solvent in an eluting solvent vessel 36. A switching valve 38 is for switching a flow path so as to selectively allow any of solutions in the three vessels 32, 34, and 36 to flow into a supply flow path 42. On the supply flow path 42, a solution sending pump 40 for taking in and sending out the solution at a predetermined flow rate is provided.

A trap column 44 is connected on a downstream side of the solution sending pump 40 on the supply flow path 42. The trap column 44 is filled with an adsorbent for trapping the target compound. The trap column 44 is disposed with its axial direction oriented in a vertical direction and the flow path is connected to the trap column 44 so that a lower end side is an inlet and an upper end side is an outlet.

A discharge flow path 50 connected to an outlet end of the trap column 44 is connected to a common port of a two-way switching valve 54 mounted in a fractionating head 52. The valve 54 is for switching and connecting the common port to the other two switch ports. A fractionating flow path 56 as a solution sending flow path is connected to the one switch port of the valve 54 and a waste solution flow path 58 communicating with a waste solution port is connected to the other switch port.

A structure for supplying the solution to the fractionating flow path 56 as the solution sending flow path is the solution sending device.

Figure 2:
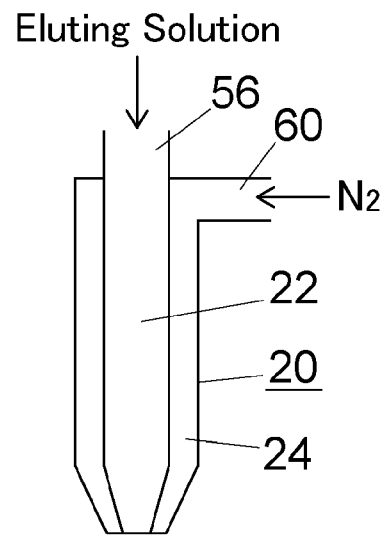
FIG. 2 is a schematic sectional view showing a probe in the embodiment.

An end of the fractionating flow path 56 is connected to the probe 20 shown in FIG. 2. A tip end portion of the probe 20 is made up of a double tube in which an inner cylindrical tube 22 is surrounded with an outer tube 24. The inner tube 22 of the double tube is connected to the fractionating flow path 56 and the outer tube 24 of the double tube is connected to the gas supply flow path 60. At a tip end portion of the double tube, an opening portion of the tip end of the double tube is in such a shape that an annular opening of the outer tube 24 surrounds and is in contact with a circular opening of the inner tube 22 with walls of both the tubes interposed therebetween.

On the gas supply flow path 60, a gas cylinder (not shown) or the like storing nitrogen gas (or another inert gas) is connected through an opening/closing valve 62.

A plurality of collecting vessels 2 for collecting the fractionated and refined target compounds are housed in a vessel rack 66 provided with a heater 68 and a temperature sensor 70 such as a thermistor. The vessel rack 66 is made of material such as aluminum having satisfactory heat conductivity and covered with heat insulating material from outside. Heat from the vessel rack 66 is transferred to the collecting vessels 2. A temperature adjusting portion 72 controls energization of the heater 68 to warm the collecting vessels 2 to a constant temperature so that a temperature detected by the temperature sensor 70 becomes a target temperature.

Figure 3:
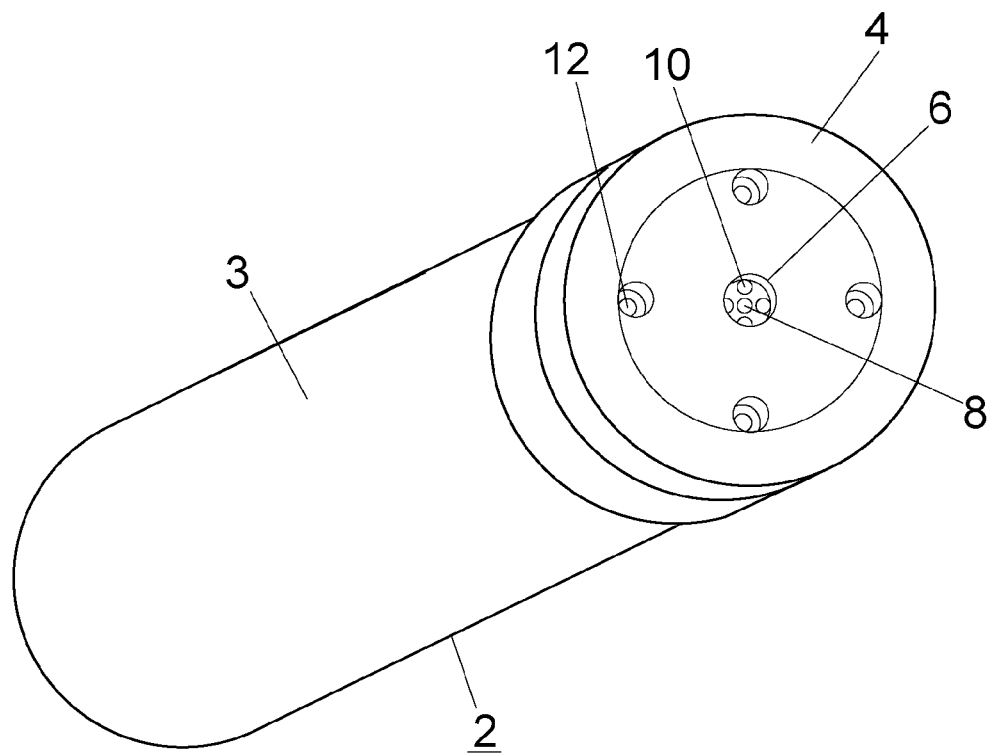
FIG. 3 is a perspective view showing a collecting vessel in the embodiment.

The collecting vessel 2 includes a cylindrical vessel main body 3 and a lid 4 which closes an opening portion of the vessel main body 3 and can be opened and closed as shown in FIG. 3. The lid 4 is in such a shape as to come in close contact with the opening portion of the vessel main body 3 and to be fitted in the opening portion of the vessel main body 3. If the opening portion of the vessel main body 3 has a screw-top structure, the lid 4 is provided with a thread to be engaged with the structure. Material of the collecting vessel 2 is for example reinforced hard glass.

Figure 4:
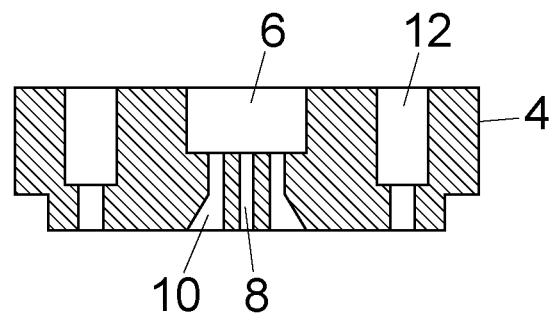
FIG. 4 is a sectional view showing a lid of the collecting vessel in the embodiment.

As shown in FIGS. 3 and 4, an inlet in which the tip end portion of the probe 20 is mounted is formed as a recessed portion 6 in the lid 4. In the recessed portion 6, a solution inlet 8 for introducing the solution from the inner tube 22 of the probe 20 into the vessel main body 3 and gas inlets 10 for introducing gas from the outer tube 24 of the probe 20 into the vessel main body 3 are open. In the lid 4, the gas discharge ports 12 connecting the inside and the outside of the vessel main body 3 are open.

The solution inlet 8 and the gas inlets 10 are positioned so that the solution inlet 8 is connected to the inner tube 22 of the probe 20 and the gas inlets 10 are connected to the outer tube 24 of the probe 20 by mounting the probe 20 to the lid 4. The solution inlet 8 is a central hole positioned at a center of the lid 4 and the gas inlets 10 are a plurality of (four, in this example) holes disposed around the solution inlet 8 and on a circumference corresponding to the annular opening at the tip end of the outer tube 24 of the probe 20. Because the opening of the inner tube 22 and the annular opening of the outer tube 24 are close to each other at the tip end portion of the probe 20, the solution inlet 8 and the gas inlets 10 are disposed in the positions close to each other as well.

A sectional shape of the hole of the gas inlet 10 widens toward the vessel main body 3 as shown in FIG. 4 and gas ejected into the vessel main body 3 from the gas inlets 10 is diffused into the vessel main body 3 to thereby nebulize the solution dropping or flowing down from the solution inlet 8.

The gas discharge ports 12 are a plurality of (four, in this example) holes and are disposed at equal intervals on a circumference outside the inlet recessed portion 6 and around the solution inlet 8 as a center.

Because the inner tube 22 of the double tube of the probe 20 is connected to the fractionating flow path 56 and the outer tube 24 of the double tube of the probe 20 is connected to the gas supply flow path 60, this example is suitable to a case in which a flow rate of the solution supplied from the fractionating flow path 56 is low. However, in an opposite manner, the inner tube 22 of the double tube of the probe 20 may be connected to the gas supply flow path 60 and the outer tube 24 of the double tube of the probe 20 may be connected to the fractionating flow path 56.

The probe 20 is fixed to the fractionating head 52 and the fractionating head 52 can be moved vertically (in a vertical direction in FIG. 1) and horizontally (in a lateral direction of a plane of FIG. 1 and a perpendicular direction to the plane) by a three-axis drive mechanism 74 including, for example, a plurality of motors and the like. The three-axis drive mechanism 74 can move the probe 20 to a position over the arbitrary collecting vessel 2 in the plurality of collecting vessels 2 housed in the vessel rack 66 through the fractionating head 52, lower the fractionating head 52 to mount the probe 20 into the recessed portion 6 in the lid 4 of the collecting vessel 2, and lift the fractionating head 52 to separate the probe 20 from the lid 4. Although the vessel rack 66 is fixed and the fractionating head 52 moves here, the fractionating head 52 may be fixed and the vessel rack 66 may move to mount the probe 20 into the arbitrary collecting vessel 2, instead.

A control portion 80 includes a CPU and the like and, according to the program set in advance, automatically carries out fractionating and refining operation by controlling switching operations of the valves 38 and 54, operation including control of the flow rate or a flow speed of the solution sending pump 40, setting of the target temperature of the temperature adjusting portion 72, movement of the fractionating head 52 through the three-axis drive mechanism 74, and the like. An operating portion 82 is for inputting and setting conditions of the fractionating and refining operation.

The automatic fractionating and refining operation in the embodiment will be described. In order to trap the target compound in the adsorbent in the trap column 44, the control portion 80 connects the solution vessel 32 and the supply flow path 42 by the switching valve 38, connects the discharge flow path 50 and the waste solution flow path 58 by the two-way switching valve 54, and operates the solution sending pump 40 to send the solution at the predetermined constant flow rate. As a result, the target compound in the solution is trapped in the adsorbent in the trap column 44.

Next, the control portion 80 switches the switching valve 38 so as to connect the cleaning water vessel 34 and the supply flow path 42 to take in the pure water in the cleaning water vessel 34 by the solution sending pump 40 and introduce it into the trap column 44. In this way, undesired and water-soluble substances such as salts which have adhered to the adsorbent in the previous trapping of the target compound are removed from an inside of the trap column 44. Because the target compound trapped in the adsorbent is hardly eluted into water due to strong adsorption action, the target compound is kept trapped in the trap column 44 at this time.

Then, by the three-axis drive mechanism 74, the control portion 80 moves the fractionating head 52 to a position over the predetermined collecting vessel 2 designated in advance and lowers the fractionating head 52 to a predetermined height to mount the probe 20 into the recessed portion 6 in the lid 4 of the collecting vessel 2. After this, the control portion 80 switches the switching valve 38 so as to connect the eluting solvent vessel 36 and the supply flow path 42 and actuates the solution sending pump 40 to introduce the dichloromethane in the eluting solvent vessel 36 into the trap column 44. The solution sending flow rate of the solution sending pump 40 is lower than that in sending the solution in the solution vessel 32 and the pure water in the cleaning water vessel 34. For example, the solution sending flow rate of the dichloromethane is about 0.5 ml/minute. The control portion 80 designates the target temperature for the temperature adjusting portion 72 and starts heating of the vessel rack 66 to start warming of the collecting vessels 2. The target temperature may be about the same as or a little higher than a boiling point of the dichloromethane and may be 40 to 45° C.

Because the dichloromethane has a higher specific gravity than water (specific gravity: 1.32), does not have compatibility with water, and is sent at the low solution sending flow rate, it flows at a low speed in the trap column 44. Therefore, if the dichloromethane is introduced into the trap column 44 from the lower end, the dichloromethane hardly mixes with the water existing in the trap column 44 and an interface between the dichloromethane and the water gradually moves up. The water pushed by the dichloromethane goes out of the upper end outlet of the trap column 44, passes through the two-way switching valve 54, and reaches the waste solution port through the waste solution flow path 58.

The control portion 80 switches the two-way switching valve 54 at a time when all the water in the flow path 50 has been discharged from the waste solution flow path 58 to introduce the dichloromethane into the fractionating flow path 56. The time at which all the water in the flow path 50 has been discharged from the waste solution flow path 58 can be calculated from a void capacity in the trap column 44 (i.e., volume of water staying in the trap column 44 immediately before introduction of the dichloromethane) and the solution sending flow rate of the dichloromethane by the solution sending pump 40. This time is calculated by the control portion 80.

The control portion 80 switches the two-way switching valve 54 to the fractionating flow path 56 side to start the fractionating of the eluting solution and opens the opening/closing valve 62 of the gas supply flow path 60 to thereby start supplying nitrogen gas through the gas supply flow path 60. If the solution sending flow rate of the dichloromethane is about 0.5 ml/minute, a suitable supply flow rate of the nitrogen gas is about 0.5 l/minute.

Figure 5:
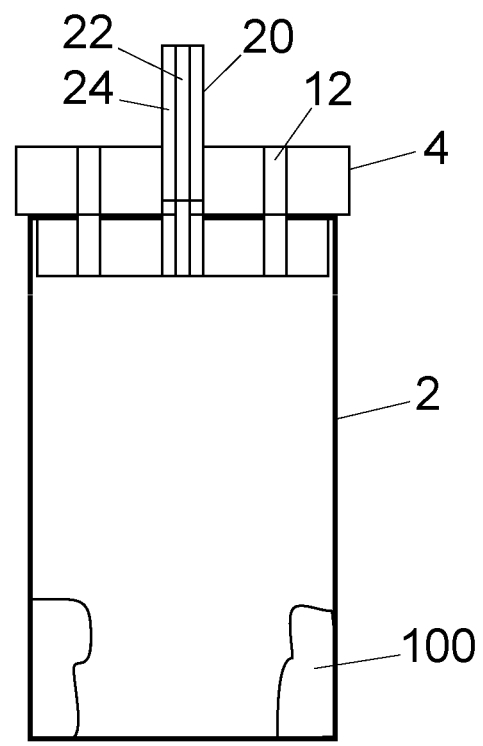
FIG. 5 is a schematic sectional view showing a target component powderized and collected in the collecting vessel in the embodiment.

Through this operation, the dichloromethane solution which is the target component drops or flows down from the solution inlet 8 of the lid 4, is nebulized by the gas ejected from the gas inlets 10 near the solution inlet 8, and is collected as powdery solid material 100 in the vessel main body 3 as shown in FIG. 5. At this time, if the dichloromethane which is the solvent does not completely evaporate and the solution adheres to an inner wall of the vessel main body 3 in the forms of droplets, the dichloromethane quickly evaporates because the vessel main body 3 is warmed. If the target component turns into powder and is stirred up by the gas in the vessel, the vessel is closed with the lid 4, and therefore, the target component does not jump out of the vessel.

Because an amount of the target compound trapped in the adsorbent in the trap column 44 is limited, a concentration of the target compound included in the eluting solution reduces when a certain amount of time has elapsed since the start of the introduction of the dichloromethane into the trap column 44. Therefore, the control portion 80 calculates the time required to finish eluting the target compound from an inner capacity (an amount of filled adsorbent) of the trap column 44 and the solution sending flow rate of the dichloromethane by the solution sending pump 40, switches the two-way switching valve 54 to the waste solution flow path 58 side again when an elapsed time from the start of the sending of the dichloromethane has reached the time obtained by the calculation, and stops the operation of the solution sending pump 40 to thereby finish the fractionating.

As described above, the fractionating and refining device according to the embodiment can quickly evaporate, online, the solvent in the solution including the target compound eluted again from the trap column 44, collect the solid target compound in the collecting vessel 2, and also suppress scattering of the powderized target component out of the collecting vessel 2.

In the embodiment, by warming the collecting vessel 2 through the vessel rack 66, evaporation of the solvent in the solution in contact with the inner wall of the vessel 2 is facilitated. If temperature of the nitrogen gas ejected from the gas supply flow path 60 into the collecting vessel 2 is high, it increases an amount of heat given to the solution to thereby further facilitate the evaporation of the solvent. Therefore, as shown in FIG. 1, for example, it is preferable to provide a heating portion 90 for heating the gas passing through the gas supply flow path 60 on the gas supply flow path 60 so that the heating portion 90 raises the temperature of the gas supplied into the collecting vessel 2. The heating portion 90 may be provided with a heater and a temperature sensor so that the control portion 80 controls the temperature to a constant temperature or may be provided with a heat exchanger through which the gas supply flow path 60 passes.

In order to similarly facilitate the evaporation of the solvent, so as to heat the eluting solution discharged from the trap column 44 and raise the temperature of the solution, it is preferable to provide a heating portion 92 for heating the solution passing through the discharge flow path 50 on the discharge flow path 50 so that the heating portion 92 raises the temperature of the solution supplied into the collecting vessel 2 as shown in FIG. 1, for example. The heating portion 92 may be provided with a heater and a temperature sensor so that the control portion 80 controls the temperature to a constant temperature or may be provided with a heat exchanger through which the discharge flow path 50 passes.

As another embodiment, a fractionating liquid chromatograph may be connected directly and the solution including the target compound and separated in the fractionating liquid chromatograph may be directly introduced into the trap column 44.

The invention claimed is:

1. A fractionating and refining device comprising:
   a solution sending device for supplying a solution including a fractionated target component from a tip end of a solution sending flow path;
   a gas supply flow path for supplying gas from a tip end thereof;
   a collecting vessel for collecting solid material of the fractionated target component, said collecting vessel comprising a lid and a vessel main body having a bottom,
   the lid closing an opening portion of the collecting vessel main body and being able to be opened and closed, and
   the lid including a solution inlet to which the tip end portion of the solution sending flow path is connected and through which the solution is supplied into the vessel main body, a gas inlet to which the tip end portion of the gas supply flow path is connected and through which the gas from the gas supply flow path is supplied into the vessel main body, and a gas discharge port connecting an inside and an outside of the vessel main body;
   a warming mechanism for warming the collecting vessel to such a temperature as to facilitate evaporation of a solvent in the solution in the collecting vessel; and
   a probe formed by integrating the tip end portion of the solution sending flow path and the tip end portion of the gas supply flow path with each other, wherein the solution inlet and the gas inlet in the lid are disposed in positions respectively corresponding to the tip end portion of the solution sending flow path and the tip end portion of the gas supply flow path integrated in the probe so that the tip end portion of the solution sending flow path and the tip end portion of the gas supply flow path are respectively connected to the solution inlet and the gas inlet in the lid when the probe is mounted to the lid,
   wherein the lid has a recessed portion, in which the solution inlet and the gas inlet are open, for mounting the probe therein to detachably connect to detachably place an end surface of the tip end portion of the solution sending flow path in contact with an end surface of the solution inlet and to detachably place an end surface of the gas supply flow path in contact with an end surface of the gas inlet.

2. The fractionating and refining device according to claim 1, wherein
   the tip end portion of the probe is made up of a concentrically arranged double tube and one tube of the double tube is connected to the solution sending flow path and the other is connected to the gas supply flow path and
   the solution inlet and the gas inlet in the lid are formed as one central inlet disposed at a center of the lid and corresponding to a central outlet of the double tube and a plurality of outer inlets disposed around the central inlet and on a circumference corresponding to an outer outlet of the double tube.

3. The fractionating and refining device according to claim 2, wherein
the inner tube of the double tube is connected to the solution sending flow path and the outer tube of the double tube is connected to the gas supply flow path.

4. The fractionating and refining device according to claim 2, wherein
a plurality of gas discharge ports are provided in the lid and disposed at equal intervals on a circumference outside the circumference on which the outer inlets are disposed.

5. The fractionating and refining device according to claim 1, comprising means for gas heating on the gas supply flow path.

6. The fractionating and refining device according to claim 1, comprising means for solution heating on the solution sending flow path.

* * * * *